(12) United States Patent
Oshima (10) Patent No.: US 8,014,489 B2
(45) Date of Patent: Sep. 6, 2011

(54) RADIOGRAPHIC IMAGING APPARATUS AND METHOD FOR CONTROLLING THE SAME

(75) Inventor: Koji Oshima, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 117 days.

(21) Appl. No.: 12/186,960

(22) Filed: Aug. 6, 2008

(65) Prior Publication Data

US 2009/0041180 A1 Feb. 12, 2009

(30) Foreign Application Priority Data

Aug. 9, 2007 (JP) ................................. 2007-208472

(51) Int. Cl.
*A61B 6/00* (2006.01)
(52) U.S. Cl. .......................................................... 378/8
(58) Field of Classification Search .................... 378/4, 8
See application file for complete search history.

(56) References Cited

U.S. PATENT DOCUMENTS

| 5,271,055 | A | * | 12/1993 | Hsieh et al. | 378/95 |
| 5,485,371 | A | * | 1/1996 | Ito et al. | 378/20 |
| 5,602,891 | A | * | 2/1997 | Pearlman | 378/62 |
| 6,236,705 | B1 | * | 5/2001 | Stergiopoulos et al. | 378/8 |
| 6,393,097 | B1 | * | 5/2002 | Aufrichtig et al. | 378/98.11 |
| 6,934,357 | B2 | * | 8/2005 | Boyd et al. | 378/62 |
| 7,230,262 | B2 | | 6/2007 | Sendai | |
| 2003/0161435 | A1 | * | 8/2003 | Ozaki | 378/4 |
| 2006/0025672 | A1 | | 2/2006 | Sendai | |
| 2006/0188058 | A1 | * | 8/2006 | Bruder | 378/8 |
| 2007/0053483 | A1 | * | 3/2007 | Nagata et al. | 378/8 |
| 2007/0116172 | A1 | * | 5/2007 | Hsieh et al. | 378/8 |
| 2009/0310737 | A1 | * | 12/2009 | Forthmann et al. | 378/8 |

FOREIGN PATENT DOCUMENTS

| JP | 05-192319 A | 8/1993 |
| JP | 2003-245272 A | 9/2003 |
| JP | 2004-073490 A | 3/2004 |
| JP | 2005-342088 A | 12/2005 |
| JP | 2006-034579 A | 2/2006 |
| WO | WO 2006067671 A2 * | 6/2006 |

OTHER PUBLICATIONS

Manzke et al., Automatic phase point determination for cardiac CT imaging, Medical Imaging: Image Processing, Proceedings of SPIE, vol. 5370, 2004, pp. 690-700.*

* cited by examiner

Primary Examiner — Edward J Glick
Assistant Examiner — Alexander H Taningco
(74) Attorney, Agent, or Firm — Canon U.S.A., Inc. I.P. Division (57) ABSTRACT

In a radiographic imaging apparatus capable of performing a first imaging in which radiographic imaging is performed with a first X-ray dose and a second imaging in which radiographic imaging is performed at a second X-ray dose that is less than the first X-ray dose, the timing corresponding to a particular phase of a periodically moving organ as a subject to be imaged is predicted, and the first imaging performed at the predicted timing and the second imaging performed a predetermined number of times before and after the predicted timing are repeated. Through this repetition, a shift between the timing of the particular phase that is recognized from images acquired through the execution of the first imaging and the second imaging and the predicted timing is detected, and the predicted timing is corrected based on the detected shift.

9 Claims, 11 Drawing Sheets

RADIOGRAPHIC IMAGING APPARATUS AND METHOD FOR CONTROLLING THE SAME

BACKGROUND OF THE INVENTION

1. Field of the Invention

The present invention relates to moving image capture using a radiographic imaging apparatus, and more particularly is suitable for capturing moving images of a periodically moving tissue such as the heart or lungs.

2. Description of the Related Art

In recent years, X-ray fluoroscopy diagnostic apparatuses for medical use that employ a method in which a diagnosis is performed using digital images rather than analog images are being increasingly used. This trend has allowed digital images that are continuously produced by radiographic imaging to be used for diagnosis, treatment and so on by displaying the digital images on a monitor as moving image data, or saving the digital images in a memory or hard disk drive.

Ordinarily, when radiographic imaging is performed to capture moving images of the chest or abdominal region of a subject, changes of an organ and so on that are caused by breathing or heart beating of the subject need to be considered to improve the accuracy of captured images. For example, the depth from the surface to an organ of a subject always varies periodically by autonomic activity of breathing. Accordingly, in order to capture images of an organ with stable accuracy with an appropriate X-ray irradiation dose, it is very important to irradiate X-rays in a state in which the depth from the surface to an organ of a subject is kept at a predetermined value (position). Furthermore, in order to obtain accurate diagnostic images, radiographic imaging is performed when the radiographic range of an organ, such as the heart or lungs, is the largest. In the case of the lungs, for example, radiographic imaging is performed when a subject inhales the maximum amount of air, or in some cases, radiographic imaging is performed continuously in each respiratory phase. In this case, the subject can hold in a particular state during the radiographic imaging by fixing his/her body and stop breathing when an instruction is given by an X-ray technician. Similarly, in the case of the heart, it is necessary to perform radiographic imaging continuously in each respiratory phase synchronized with heat beating. Accordingly, it is important to perform radiographic imaging according to the motion of the subject. In this case, however, it is impossible to stop the heart.

In view of the foregoing, various methods have been proposed to achieve X-ray moving image capture performed in synchronization with a desired phase by detecting the phase of a periodically moving tissue, such as the heart or lungs, of a subject using some kind of means.

Japanese Patent Laid-Open Nos. H5-192319 and 2004-073490 propose a method for performing radiographic imaging according to the motion of a subject, where the frame rate for moving images or the intensity of X-ray pulses is made variable according to the motion.

As a proposal regarding radiographic imaging performed in synchronization with the motion of a subject, particularly in synchronization with the phase, in Japanese Patent Laid-Open Nos. 2003-245272, 2005-342088 and 2006-034579, methods have been proposed in which X-ray moving image capture is performed in synchronization with a desired phase obtained through detection of the cycle of a moving tissue by analyzing diagnostic fluoroscopy images of a subject or by using an external factor such as a positional shift of the body surface of the subject.

However, an X-ray diagnostic apparatus that performs radiographic imaging at a timing synchronized with the motion phase of a periodically moving tissue, such as the heart or lungs, employs X-ray moving images for fluoroscopic diagnosis to detect the phase. The X-ray moving images for fluoroscopic diagnosis are captured by irradiating X-ray pulses at a strong dose that is necessary for fluoroscopic diagnosis. Usually, the frame rate is required to be increased to synchronize with the motion phase, but if X-ray moving images for fluoroscopic diagnosis are captured at a high frame rate, the amount of radiation exposure to the subject increases. Conversely, if the frame rate is lowered to reduce the amount of radiation exposure to the subject, radiographic imaging cannot be performed in synchronization with the motion phase, and thus this is problematic in that radiographic imaging cannot be performed at an optimal timing.

SUMMARY OF THE INVENTION

According to one aspect of the present invention, a radiographic imaging apparatus includes an imaging unit configured to perform a first imaging in which radiographic imaging is performed with a first X-ray dose and a second imaging in which radiographic imaging is performed at a second X-ray dose that is less than the X-ray first dose, an execution unit configured to execute the first imaging on a periodically moving organ at a timing predicted to correspond to a particular phase in a cycle of the periodically moving organ and to execute the second imaging at a predetermined frequency before and after the predicted timing, a detection unit configured to detect a shift between a timing corresponding to the particular phase that is recognized based on images acquired through the first and second imagings and the predicted timing, and a correction unit configured to correct the predicted timing based on the shift.

Further features of the present invention will become apparent from the following description of exemplary embodiments with reference to the attached drawings.

DESCRIPTION OF THE EMBODIMENTS

Exemplary embodiments of the present invention will now be described in detail in accordance with the accompanying drawings.

Figure 1:
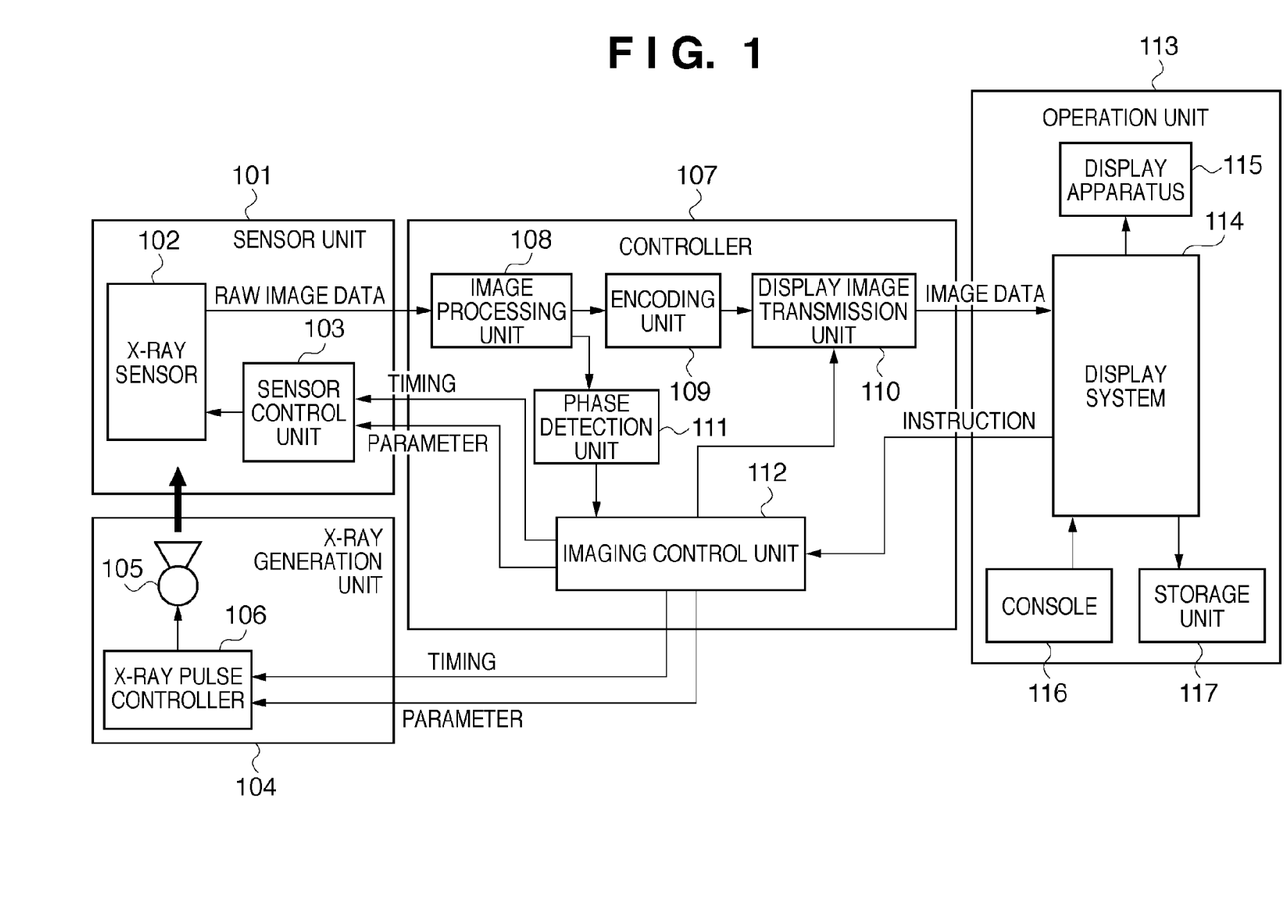
FIG. 1 is a block diagram illustrating an example of the configuration of an X-ray fluoroscopy diagnostic apparatus according to an embodiment of the present invention.

FIG. 1 is a block diagram illustrating the overall configuration of an X-ray fluoroscopy diagnostic apparatus according to an embodiment of the present invention. The X-ray fluoroscopy diagnostic apparatus shown in FIG. 1 includes a sensor unit 101, an X-ray generation unit 104, a controller 107, and an operation unit 113.

The sensor unit 101 includes an X-ray sensor 102 and a sensor control unit 103. The X-ray sensor 102 includes a solid-state imaging device that can respond to X-rays and convert/output into electric signals corresponding to the intensity of detected X-rays. Alternatively, the X-ray sensor 102 may be a unit obtained by combining a fluorescent material that generates visible light corresponding to the energy of X-rays and a photoelectric conversion device that converts the visible light to an electric signal corresponding to the intensity of the visible light.

Raw image digital data output from the X-ray sensor 102 is sent to the controller 107. The sensor control unit 103 performs sensor drive control such as generating a data output timing signal for the X-ray sensor 102 in accordance with a timing instruction from an imaging control unit 112, and setting sensor's output mode. A high-speed digital interface such as LVDS (Low Voltage Differential Signaling) is used for data transfer between the sensor unit 101 and the controller 107. To input and output parameters, an asynchronous serial communication, such as UART (Universal Asynchronous Receiver-Transmitter), is used.

The X-ray generation unit 104 includes an X-ray tube 105 and an X-ray pulse controller 106. The X-ray tube 105 radiates pulse X-rays in response to a timing signal from the X-ray pulse controller 106. The X-ray pulse controller 106 performs processing to output an X-ray radiation timing signal to the X-ray tube 105 under set radiation conditions in response to a timing instruction from an imaging control unit 112 or a set parameter.

The controller 107 includes an image processing unit 108, an encoding unit 109, a display image transmission unit 110, a phase detection unit 111, and the imaging control unit 112. To input and output parameters between the X-ray generation unit 104 and the controller 107, an asynchronous serial communication or low latency network protocol such as CAN (Controller Area Network) is used. The present embodiment is not limited to this type of network protocol and any protocol that would enable practice of the present invention is applicable.

Sending a timing instruction continuously to the X-ray generation unit 104 and the sensor unit 101 enables continuous imaging of X-ray fluoroscopic images. For example, if 30 timing instructions are given per second, moving image data can be generated at 30 fps. Ordinarily, an X-ray fluoroscopy diagnostic apparatus can perform continuous imaging at a frame rate of 30 to 100 fps. Even the heart, which moves relatively fast compared to other organs, repeats expansion and contraction at intervals of about one second, and therefore no particular problem arises if image data can be generated at 30 fps.

The image processing unit 108 performs a predetermined image process upon receiving the raw image digital data output from the sensor unit 101. The image process includes image quality improving processes, such as correction and noise removal, depending on the characteristics of the X-ray sensor and improvement of dynamic range. The image processing unit 108 also sends the image-processed data to the phase detection unit 111, and at the same time, sends image data captured for diagnosis from the image-processed data, that is, display image data to the encoding unit 109. The encoding unit 109 performs a lossless compression/encoding process on the image-processed display image data, and sends the resultant to the display image transmission unit 110. The controller 107 and the operation unit 113 are connected, for example, via a gigabit Ethernet-based network. The display image transmission unit 110 converts the image data into packets and executes a network protocol process, and then sends the data to the operation unit 113 via the network. The present embodiment is not limited to this type of network, and any network that would enable practice of the present invention is applicable.

The phase detection unit 111 determines an X-ray irradiation timing at which a diagnostic image is captured (hereinafter referred to as "main imaging") and an X-ray irradiation timing at which an image used for motion detection is captured (hereinafter referred to as "auxiliary imaging"). The main imaging is performed on periodically moving tissue, such as the heart or lungs, in synchronization with a desired phase. For example, imaging is continuously performed on the heart in the state in which the heart expands the most in the expansion and contraction motion of the heart caused by heart beating. Imaging is also continuously performed on the lungs when the subject inhales the maximum amount of air. The auxiliary imaging is performed before and after the main imaging such that the main imaging is performed at an appropriate phase. A shift in phase is detected from the amount of motion of the image data of the captured images, and the timing of the main imaging is corrected. The image data obtained by the auxiliary imaging is used to detect motion and is typically not used for diagnosis, and thus high definition images are not necessary. Accordingly, it is sufficient to use X-ray pulses at a dose lower than that of the X-ray pulses used by the main imaging. The X-ray irradiation timing for the main imaging and the X-ray irradiation timing for auxiliary imaging are transmitted to the imaging control unit 112. The operation of the phase detection unit 111 is described below.

The imaging control unit 112 sends a timing instruction or a parameter instruction to the sensor unit 101 and the X-ray generation unit 104 in response to each X-ray irradiation timing from the phase detection unit 111, or in accordance with the imaging conditions based on an instruction from the operation unit 113.

The operation unit 113 includes a display system 114, a display apparatus 115, a console 116, and a storage unit 117. In the present embodiment, the operation unit 113 includes a personal computer (PC) and peripherals that are connected to the PC. The display system 114 can be realized by, for example, the PC itself and application software running on the PC. The display system 114 receives encoded image data sent from the controller 107, decodes the data, and outputs the results to the display apparatus 115 or stores it in the storage unit 117. In response to operations from the console 116, the display system 114 also sends various instructions to the controller 107 such as start/stop imaging and setting image mode.

The operation of periodically moving tissue, such as the heart or lungs, will be described next. The following descriptions describe the expansion and contraction motion of the lungs with reference to FIGS. 2 and 3.

Figure 2:
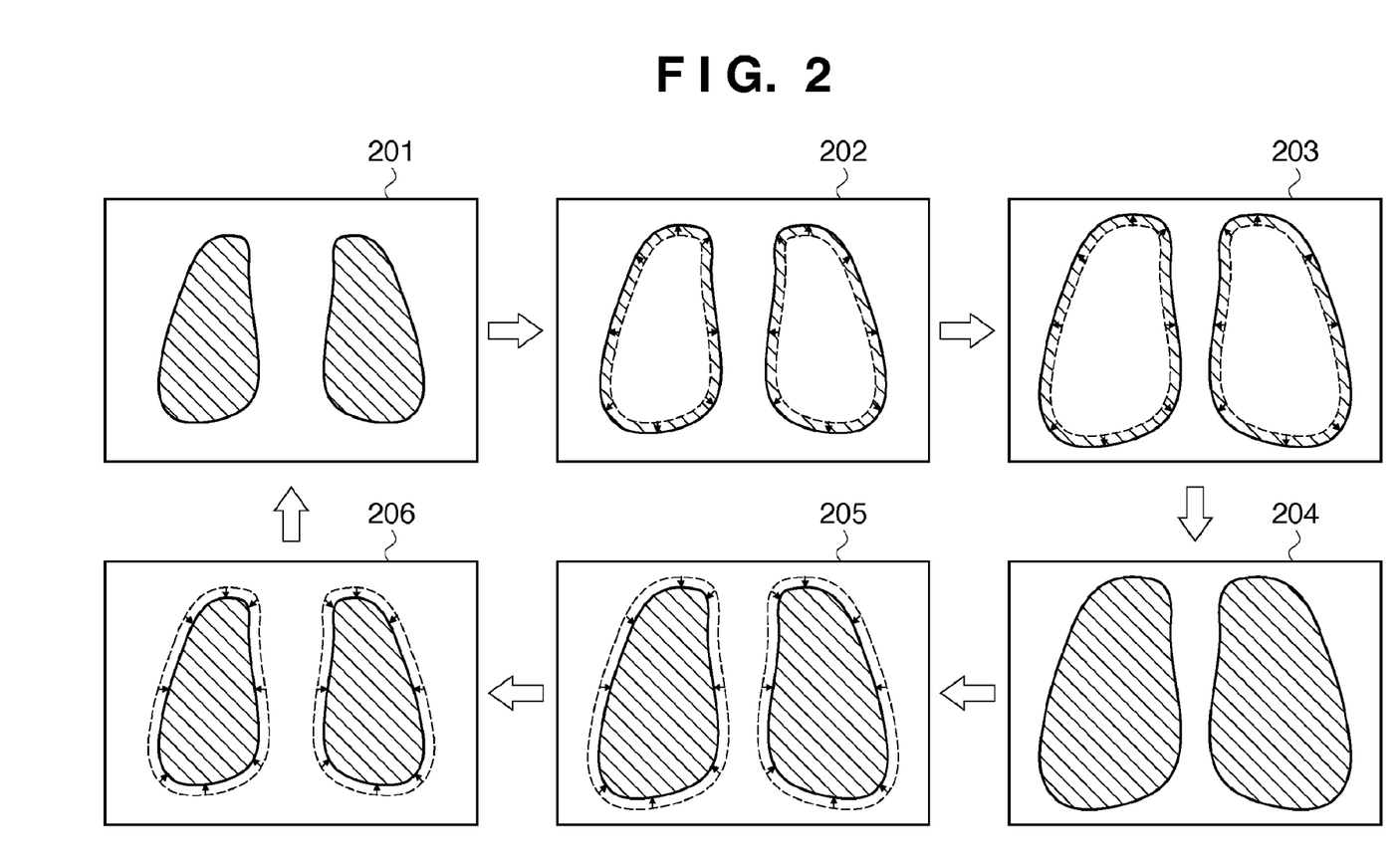
FIG. 2 is a diagram used to illustrate the expansion and contraction motion of the lungs.

FIG. 2 is a diagram illustrating an expansion and contraction motion of the lungs that occurs when a subject breathes. In FIG. 2, reference numeral 201 shows the most contracted state of the lungs, and 204 shows the most expanded state of the lungs. When the subject inhales, the lungs continue to expand gradually from the state in 201, through the states in 202 and 203, to the most expanded state in 204. Conversely, when a subject exhales, the lungs continue to contract gradually from the state in 204, through the states in 205 and 206, to the most contracted state in 201. As described above, when the subject breathes, the lungs always perform periodic autonomic activity by sequentially repeating the expansion and contraction motion ranging from states 201 to 206.

Figure 3:
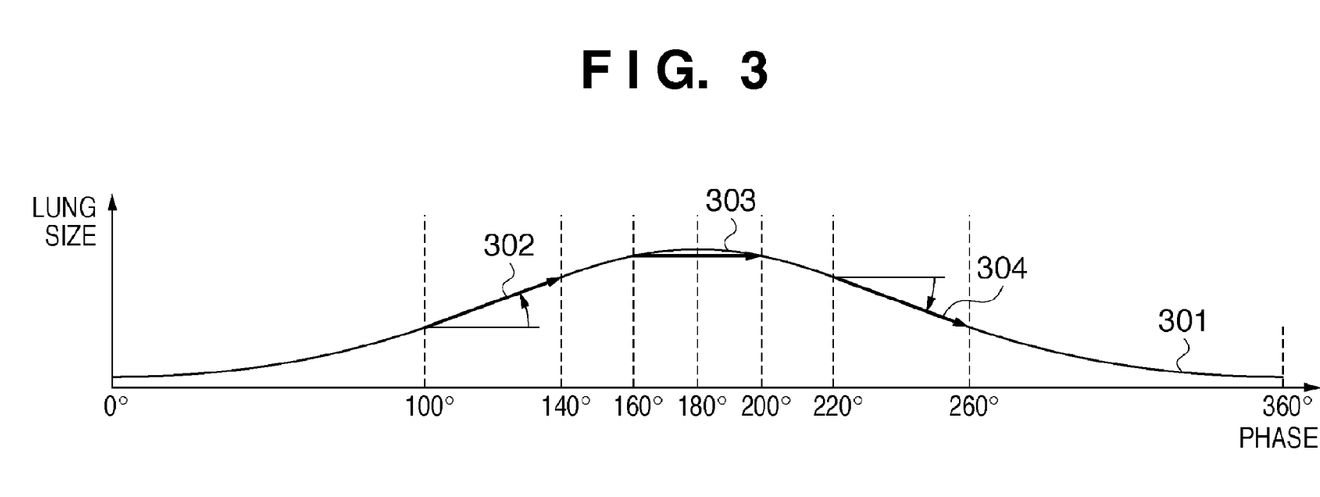
FIG. 3 is a graph obtained based on the expansion and contraction motion of the lungs shown in FIG. 2.

FIG. 3 is a graph based on the expansion and contraction motion of the lungs shown in FIG. 2. In FIG. 3, the horizontal axis represents a normalized single expansion/contraction cycle of the lungs ranging from the most contracted state to the next same state (the most contracted state), which is expressed in phases ranging from 0° to 360°. The vertical axis represents the lung size. The amount of increase or decrease in lung size corresponds to the area of a screen (the number of pixels). More specifically, the lungs are most contracted at phases of 0° and 360°, which correspond to state 201. The lungs are most expanded at a phase of 180°, which corresponds to state 204. FIG. 3 further shows the relationship between the phase of expansion and contraction motion of the lungs and the amount of change. Specifically, the arrow 302 of FIG. 3 indicates the amount of change in lung size between the phases of 100° and 140°. Arrow 302 points in the direction of increase, thus depicting that the lungs are expanding. Similarly, arrow 304 indicates the amount of change in lung size between the phases of 220° and 260°. Arrow 304 points in the direction of decrease, thus depicting the lungs are contracting. Arrow 303 indicates the amount of change in lung size between the phases of 160° and 220°. Since arrow 303 points in the horizontal direction without any increase or decrease, the lungs are most expanded during this time (or the time at which the lungs are most expanded is included). By modeling the motion of the periodically moving tissue, such as the heart and lungs, as a relationship between the phase and the amount of change, it is possible to determine the current state of the tissue.

The operation of the phase detection unit 111 will be described next with reference to FIGS. 4 to 10B.

Figure 4:
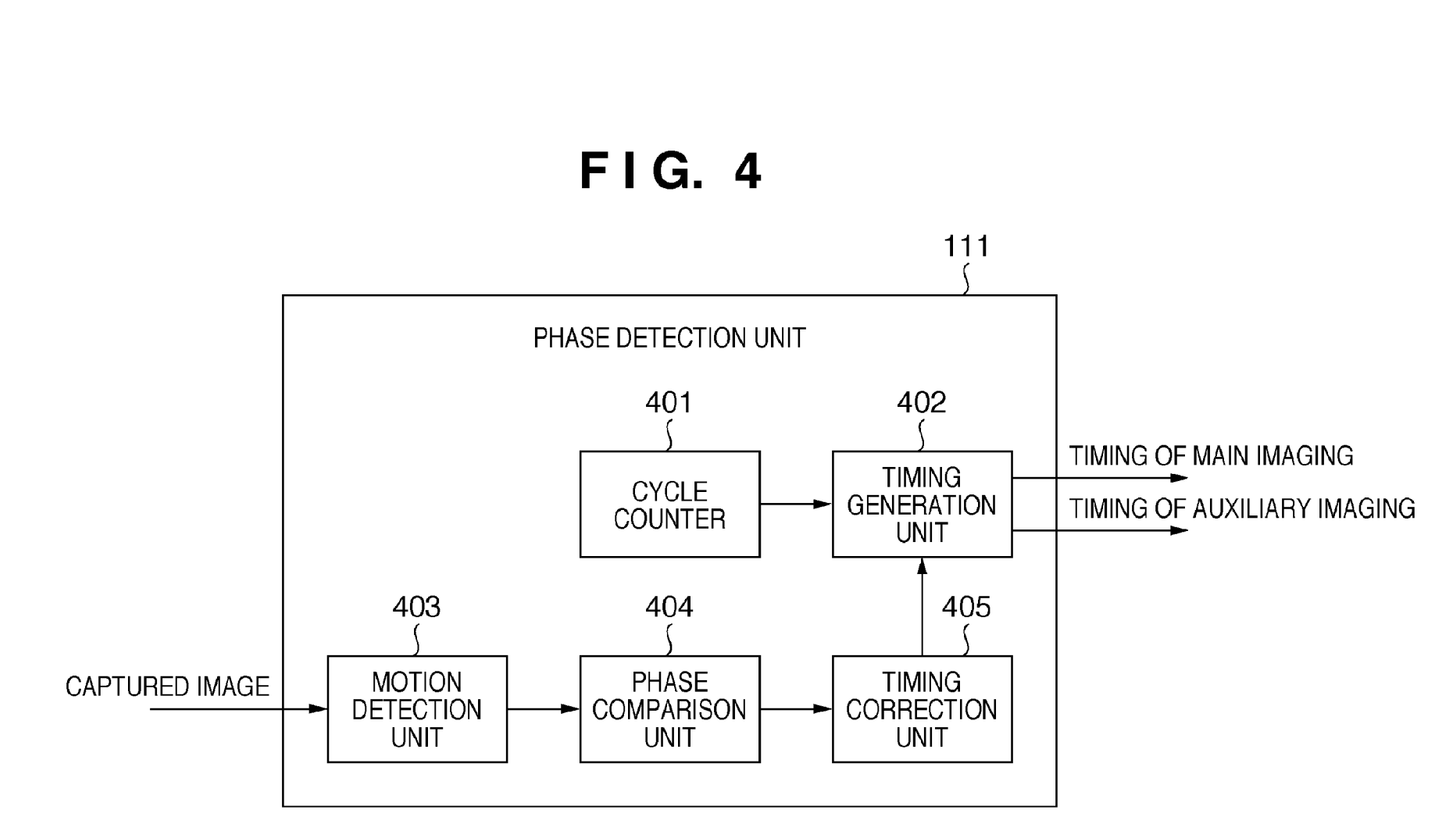
FIG. 4 is a block diagram illustrating an example of the configuration of a phase detection unit 111 according to an embodiment of the present invention.

FIG. 4 is a block diagram illustrating the overall configuration of the phase detection unit 111. The phase detection unit 111 includes a cycle counter 401, a timing generation unit 402, a motion detection unit 403, a phase comparison unit 404, and a timing correction unit 405.

The cycle counter 401 is a counter that performs counting at a preset internal timing within a single cycle of the motion of the object to generate the X-ray irradiation timing for main imaging and the X-ray irradiation timing for auxiliary imaging. The cycle counter 401 resets its counter value to zero for each cycle, and repeats counting, and thus, as long as the motion of the object is constant, the phase of the object matches the counter value. The value of the cycle counter 401 is input to the timing generation unit 402.

The timing generation unit 402 generates the X-ray irradiation timing for main imaging and the X-ray irradiation timing for auxiliary imaging according to the output values of the cycle counter 401 based on instructions from the timing correction unit 405. The timing correction unit 405 associates a predicted phase of the subject at which an image is obtained by main imaging with a value of the cycle counter 401, determines the frequency of auxiliary imaging, and associates respective predicted phases of the subject at which an image is obtained by auxiliary imaging with a value of the cycle counter 401, and then sends an instruction to the timing generation unit 402. The timing generation unit 402 generates respective X-ray irradiation timings at the values of the cycle counter 401 based on the instructions from the timing correction unit 405, thereby generating timings at which the subject is imaged at the predicted phases.

The motion detection unit 403 calculates the direction and size of motion vector of the object based on the image data obtained by the main imaging and the auxiliary imaging. The calculation of the motion vector is performed, for example, on a macroblock basis, and by combining them, it is possible to calculate whether the motion of the entire object is in the direction of expansion or in the direction of contraction, or the amount of increase or decrease thereof. The algorithms used for such motion detection are widely used in conventional technology, thus, detailed descriptions thereof are omitted here.

The phase comparison unit 404 determines whether the current imaging timing (predicted phase of the main imaging) at which a main imaging image is obtained is delayed or advanced relative to the actual phase based on the direction and size of the motion vector calculated in the motion detection unit 403. For example, the amount of increase and the amount of decrease of the motion vector are added together, and if the result is 0, it is determined that the predicted phase and the actual phase are equal. If the result is positive, it is determined that the predicted phase is advanced relative to the actual phase. If the result is negative, it is determined that the predicted phase is delayed relative to the actual phase. Furthermore, the phase comparison unit 404 calculates the amount of correction of the imaging timing from the result of the addition, and transmits the resultant to the timing correction unit 405.

The timing correction unit 405 updates, based on a comparison result of the phase comparison unit 404, the association between the predicted phase of the subject at which a main imaging image is obtained and the value of the cycle counter 401, the frequency of auxiliary imaging, and each association between the predicted phase of the subject at which each auxiliary imaging image is obtained and the value of the cycle counter 401. Specifically, if the predicted phase of the subject is delayed relative to the actual phase, each association between a predicted phase and a value is updated such that imaging is performed at a timing earlier than the current values of the cycle counter 401. If the predicted phase of the subject is advanced relative to the actual phase, each association between a predicted phase and a value is updated such that imaging is performed at a timing later than the current values of the cycle counter 401. If the predicted phase of the subject is equal to the actual phase, each association is not updated. Furthermore, the timing correction unit 405 updates the frequency of auxiliary imaging according to the amount of correction of the imaging timing from the phase comparison unit 404. Specifically, if the amount of correction is large, imaging may not sufficiently be following the motion of the object. Accordingly, the frequency of auxiliary imaging is increased to improve the accuracy. Conversely, if the amount of correction is small, it is deemed that imaging is sufficiently following the motion of the object, so that the frequency of auxiliary imaging is decreased to reduce the amount of radiation exposure. However, it is assumed that auxiliary imaging is performed at least once.

FIGS. 5A and 5B to FIGS. 7A and 7B are diagrams illustrating an example of the processes performed by the phase detection unit 111. The following description is given of the case of the expansion and contraction motion of the lungs described in FIG. 3. Specifically, the lungs are most contracted at phases of 0° and 360°, and the lungs are most expanded at a phase of 180°. It is assumed that main imaging is performed continuously in synchronization with a phase of 180° in which the lungs are most expanded.

Figure 5A:
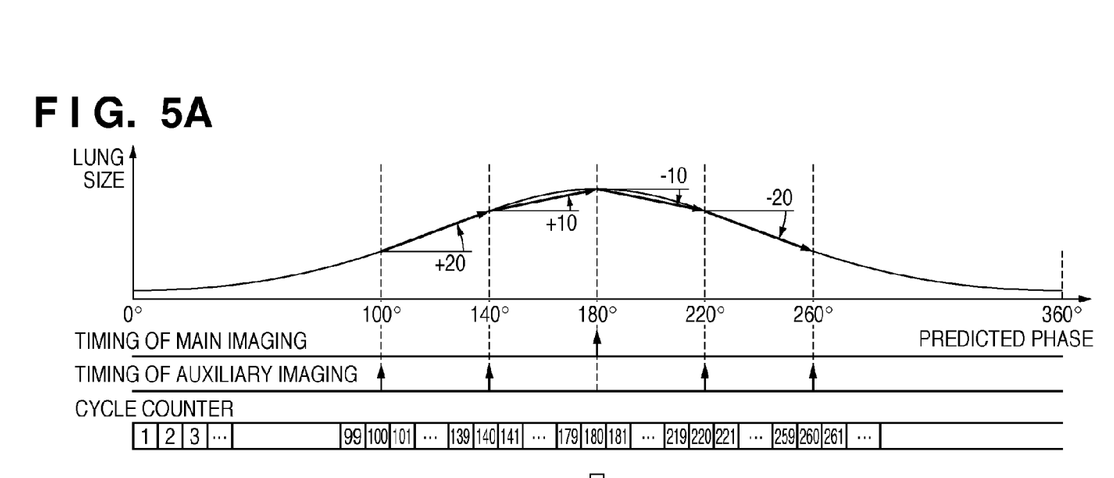
FIGS. 5A and 5B are diagrams used to illustrate an operation performed by a phase detection unit of the embodiment when a predicted phase of the lungs is equal to the actual phase.
Figure 5B:
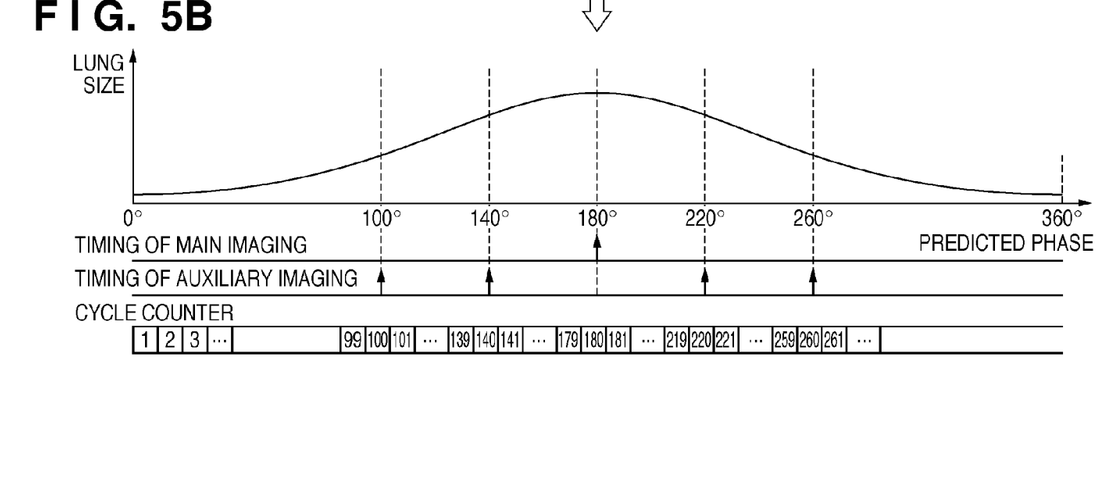

FIG. 5A is a diagram illustrating when the predicted phase of the lungs and the actual phase are equal. The timing generation unit 402 generates the X-ray irradiation timing for main imaging at a phase of 180° as a predicted phase. The timing generation unit 402 also generates the X-ray irradiation timing for auxiliary imaging at phases of 100°, 140°, 220° and 260°. Accordingly, the auxiliary imaging is executed at timings symmetric with respect to the phase of 180° at which main imaging is performed. The phase comparison unit 404 compares the predicted phase of the lungs and the actual phase thereof using the motion vector calculated based on the image data obtained from the main imaging and the auxiliary imaging. Referring to FIG. 5A, the amount of increase and the amount of decrease in lung size are +20, +10, −10 and −20. If these are added together, 0 is obtained. Accordingly, the phase comparison unit 404 determines that the predicted phase and the actual phase are equal. Thus, the timing correction unit 405 does not update the association between the predicted phase and the value of the cycle counter 401, and imaging is performed at the same timings for the next cycle. FIG. 5B shows the imaging timing in the subsequent cycle.

Figure 6A:
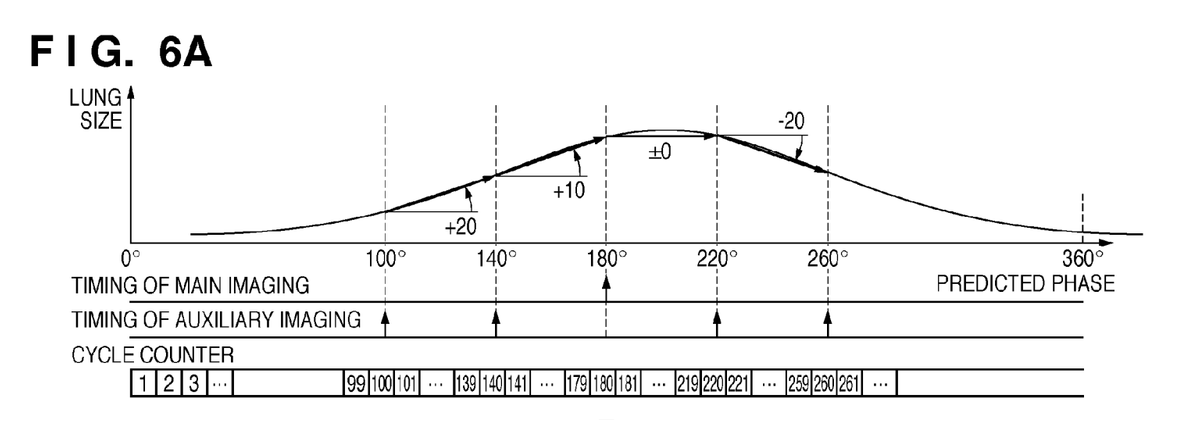
FIGS. 6A and 6B are diagrams used to illustrate an operation performed by a phase detection unit of the embodiment when a predicted phase of the lungs is advanced relative to the actual phase.
Figure 6B:
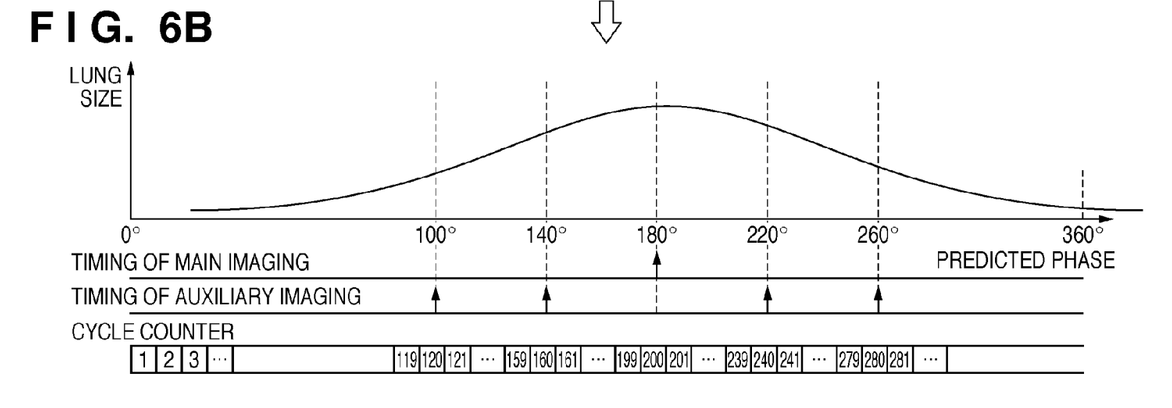

FIG. 6A is a diagram illustrating when the predicted phase of the lungs is advanced relative to the actual phase. As described above, the timing generation unit 402 generates the X-ray irradiation timing for main imaging at a phase of 180° as a predicted phase, and the X-ray irradiation timing for auxiliary imaging at phases of 100°, 140°, 220° and 260°. The phase comparison unit 404 compares the predicted phase of the lungs and the actual phase using the motion vector calculated based on the image data obtained from the main imaging and the auxiliary imaging. Referring to FIG. 6A, the amount of increase and the amount of decrease in lung size are +20, +10, 0 and −20. If these are added together, +20 is obtained. The phase comparison unit 404 determines that the predicted phase is advanced relative to the actual phase. Accordingly, the timing correction unit 405 updates the association between the predicted phase of the lungs and the values of the cycle counter 401 such that imaging is performed at a timing later than the current values of the cycle counter 401, and each imaging is performed at a timing later in the next cycle than in the current cycle. FIG. 6B shows an imaging timing in the cycle subsequent to that of FIG. 6A. Referring to FIG. 6B, in the predicted phase of the lungs, 20 cycles are added to the respective values of the cycle counter of FIG. 6A, and each X-ray irradiation timing is generated at a timing later than that of the previous cycle so as to follow the actual phase.

Figure 7A:
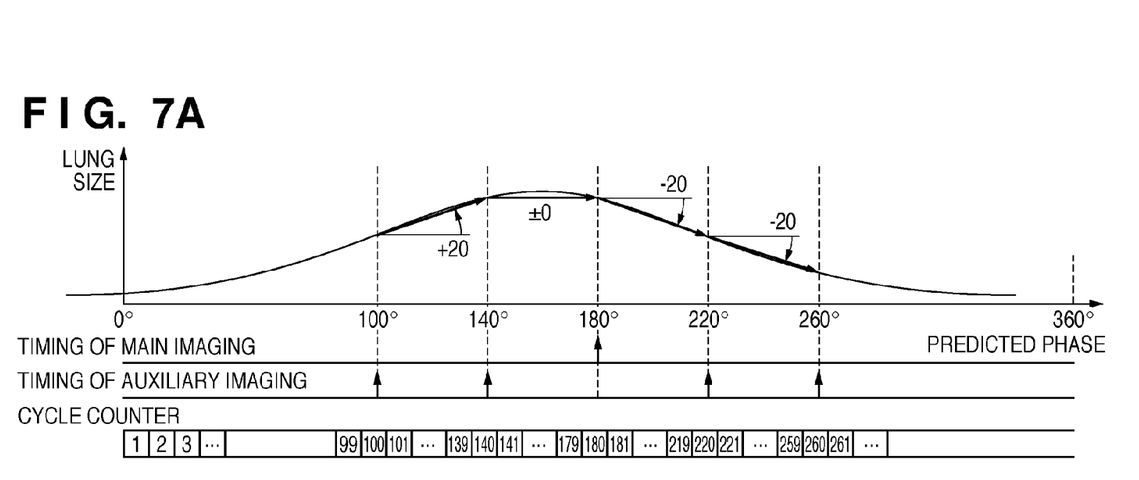
FIGS. 7A and 7B are diagrams used to illustrate an operation performed by a phase detection unit of the embodiment when a predicted phase of the lungs is delayed relative to the actual phase.
Figure 7B:
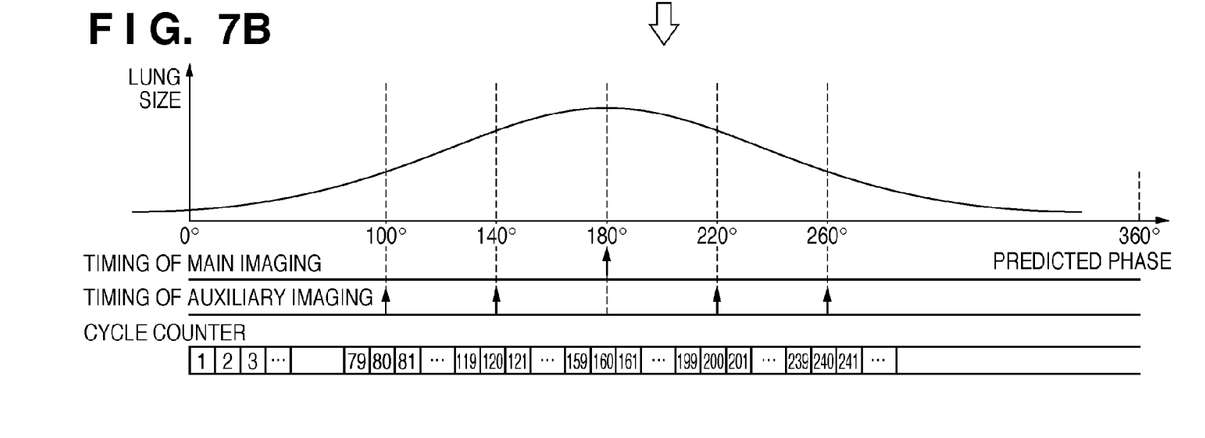

FIG. 7A is a diagram illustrating when the predicted phase of the lungs is delayed relative to the actual phase. As described above, the timing generation unit 402 generates the X-ray irradiation timing for main imaging at a phase of 180° as a predicted phase, and the X-ray irradiation timing for auxiliary imaging at phases of 100°, 140°, 220° and 260°. As described above, the phase comparison unit 404 compares the predicted phase of the lungs and the actual phase using the motion vector calculated based on the image data obtained from the main imaging and the auxiliary imaging. Referring to FIG. 7A, the amount of increase and the amount of decrease in lung size are +20, +0, −20 and −20. If these are added together, −20 is obtained. Accordingly, the phase comparison unit 404 determines that the predicted phase is delayed relative to the actual phase. Accordingly, the timing correction unit 405 updates the association between the predicted phase of the lungs and the values of the cycle counter 401 such that imaging is performed at a timing earlier than the current values of the cycle counter 401, and each imaging is performed at a timing earlier in the next cycle than in the current cycle. FIG. 7B shows an imaging timing in the cycle subsequent to that of FIG. 7A. Referring to FIG. 7B, in the predicted phase of the lungs, 20 cycles are subtracted from the respective values of the cycle counter of FIG. 7A, and each X-ray irradiation timing is generated at a timing earlier than that of the previous cycle so as to follow the actual phase.

By repeating the above process, the main imaging is performed continuously in synchronization with a phase of 180° in which the lungs are most expanded, so that even if a change occurs in the motion of the lungs during imaging, the imaging timing can be corrected to follow the motion of the lungs.

FIGS. 8A to 10B are diagrams illustrating another example of the processes performed by the phase detection unit 111. The following description is also directed to the case of the expansion and contraction motion of the lungs described in FIG. 3. Specifically, the lungs are most contracted at phases of 0° and 360°, and the lungs are most expanded at a phase of 180°. It is assumed that main imaging is performed continuously in synchronization with a phase of 180° in which the lungs are most expanded.

Figure 8A:
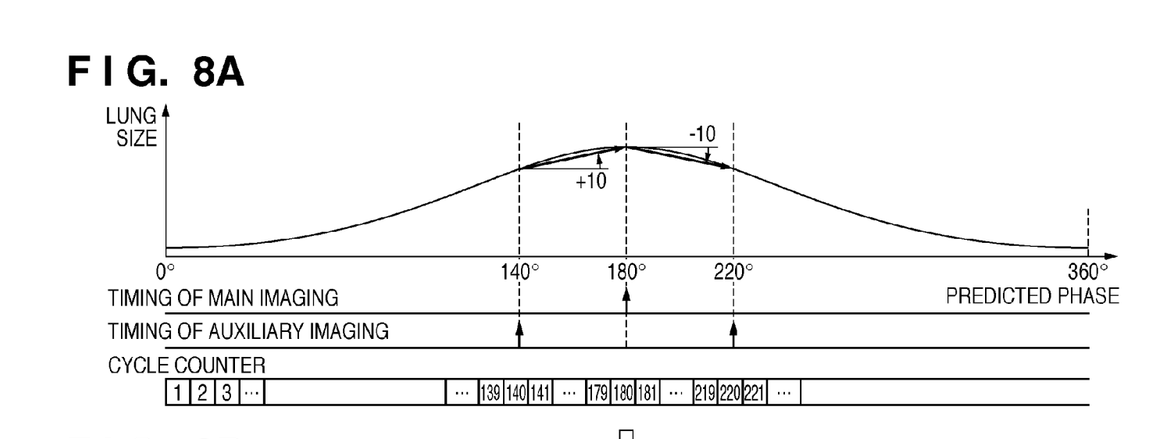
FIGS. 8A and 8B are diagrams illustrating another example of the operation performed by a phase detection unit of the embodiment when a predicted phase of the lungs is equal to the actual phase.
Figure 8B:
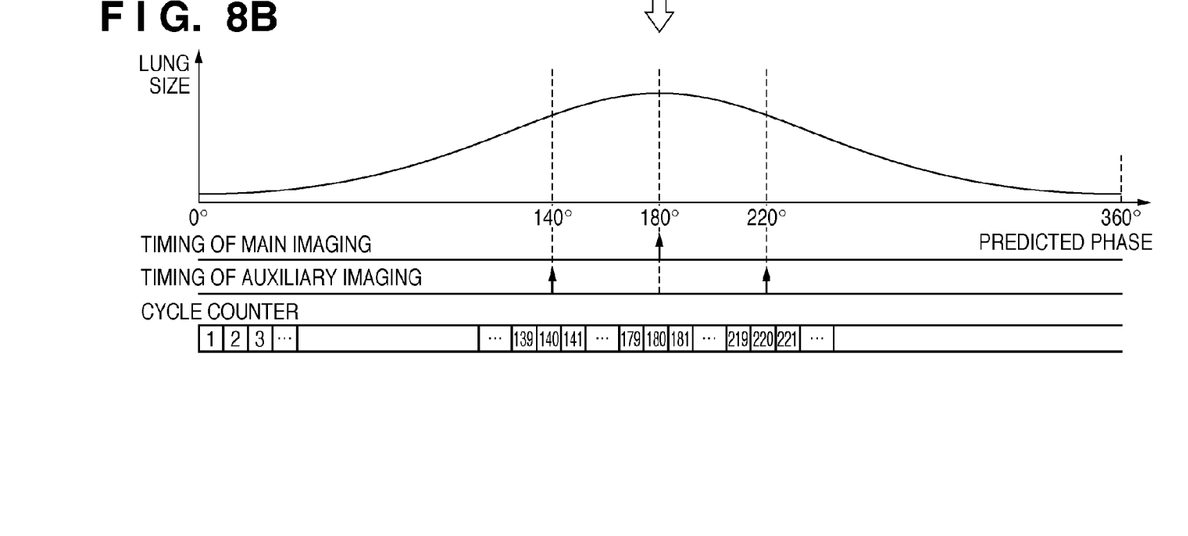

FIG. 8A is a diagram illustrating when the predicted phase of the lungs and the actual phase thereof are equal. The timing generation unit 402 generates the X-ray irradiation timing for main imaging at a phase of 180° as a predicted phase. The timing generation unit 402 also generates the X-ray irradiation timing for auxiliary imaging at phases of 140° and 220°. Accordingly, the X-ray irradiation timings for auxiliary imaging are set to be symmetric with respect to the phase of 180° at which main imaging is performed. The phase comparison unit 404 compares the predicted phase of the lungs and the actual phase using the motion vector calculated based on the image data obtained from the main imaging and the auxiliary imaging. Referring to FIG. 8A, the amount of increase and the amount of decrease in lung size are +10 and −10. If these are added together, 0 is obtained. Accordingly, the phase comparison unit 404 determines that the predicted phase and the actual phase are equal. Thus, the timing correction unit 405 does not update the association between the predicted phase and the values of the cycle counter 401, and imaging is performed at the same timings for the next cycle. FIG. 8B shows an imaging timing in the cycle subsequent to that of FIG. 8A.

Figure 9A:
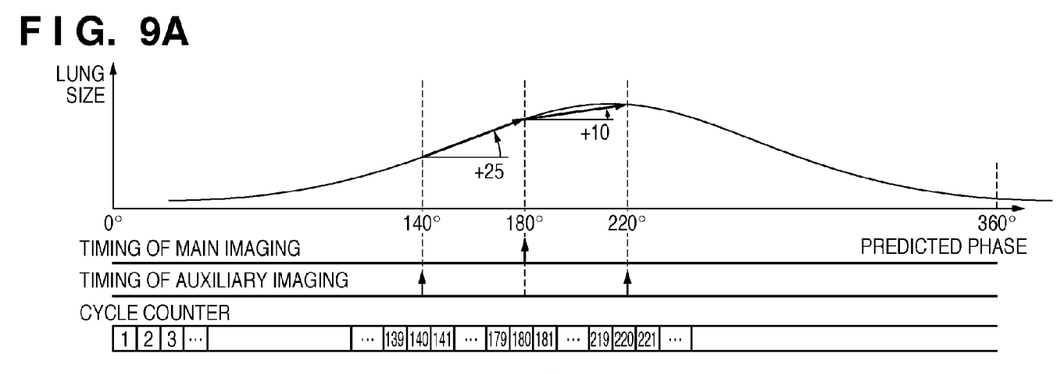
FIGS. 9A and 9B are diagrams illustrating another example of the operation performed by a phase detection unit of the embodiment when a predicted phase of the lungs is advanced relative to the actual phase.

FIG. 9A is a diagram illustrating when the predicted phase of the lungs is advanced relative to the actual phase. The timing generation unit 402 generates the X-ray irradiation timing for main imaging at a phase of 180° as a predicted phase, and the X-ray irradiation timing for auxiliary imaging at phases of 140° and 220°. The phase comparison unit 404 compares the predicted phase of the lungs and the actual phase using the motion vector calculated based on the image data obtained from the main imaging and the auxiliary imaging. Referring to FIG. 9A, the amount of increase and the amount of decrease in lung size are +25 and +10. If these are added together, +35 is obtained. Accordingly, the phase comparison unit 404 determines that the predicted phase is advanced relative to the actual phase. The phase comparison unit 404 also compares the sum and a preset value (25 in the present embodiment). In the example of FIG. 8A, the sum is greater than the preset value, and therefore the phase comparison unit 404 determines that the predicted phase of the lungs is advanced significantly relative to the actual phase. In this case, the timing correction unit 405 updates the association between the predicted phase of the lungs and the values of the cycle counter 401 such that imaging is performed at a timing later than the current values of the cycle counter 401, and at the same time, increases the frequency of auxiliary imaging.

Figure 9B:
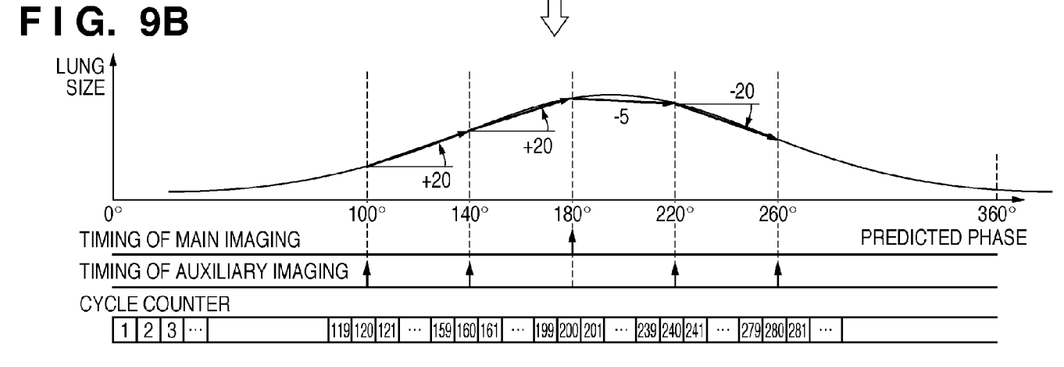

FIG. 9B shows an imaging timing in the cycle subsequent to that of FIG. 9A. Referring to FIG. 9B, in the predicted phase of the lungs, 20 cycles are added to the respective values of the cycle counter of FIG. 9A, and each X-ray irradiation timing is generated at a timing later than that of the previous cycle. Furthermore, the X-ray irradiation for auxiliary imaging is performed at phases of 100°, 140°, 220° and 260° to improve the accuracy of phase detection. Accordingly, the changed X-ray irradiation timings for auxiliary imaging are symmetric with respect to the phase of 180° at which main imaging is performed.

Figure 10A:
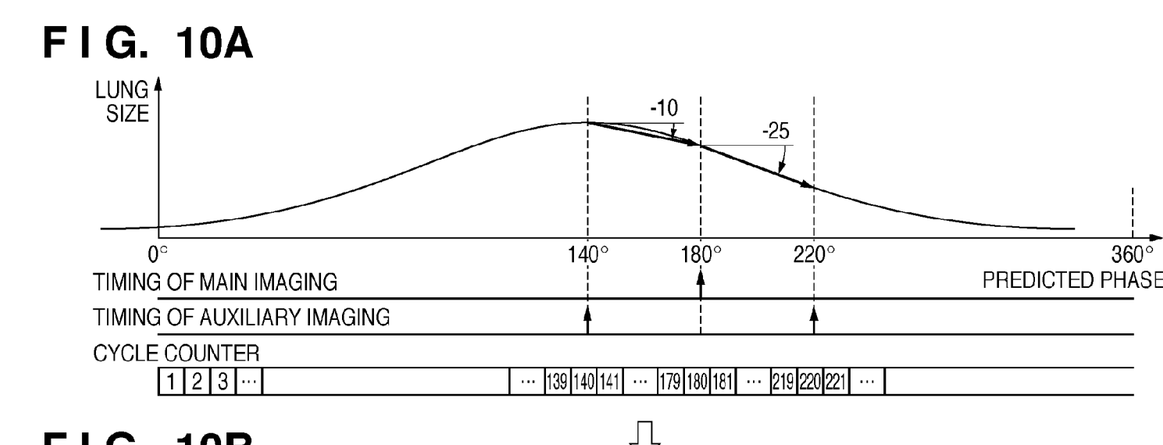
FIGS. 10A and 10B are diagrams illustrating another example of the operation performed by a phase detection unit of the embodiment when a predicted phase of the lungs is delayed relative to the actual phase.

FIG. 10A is a diagram illustrating when the predicted phase of the lungs is delayed significantly relative to the actual phase. As described above, the timing generation unit 402 generates the X-ray irradiation timing for main imaging at a phase of 180° as a predicted phase, and the X-ray irradiation timing for auxiliary imaging at phases of 140° and 220°. The phase comparison unit 404 compares the predicted phase of the lungs and the actual phase thereof using the motion vector calculated based on the image data obtained from the main imaging and the auxiliary imaging. Referring to FIG. 10A, the amount of increase and the amount of decrease in lung size are −10 and −25. If these are added together, −35 is obtained. Accordingly, the phase comparison unit 404 determines that the predicted phase is delayed relative to the actual phase. The phase comparison unit 404 also compares the sum and a preset value (−25 in the present embodiment). In the example of FIG. 10A, the sum is smaller than the preset value, and therefore the phase comparison unit determines that the predicted phase of the lungs is delayed significantly relative to the actual phase. In this case, the timing correction unit 405 updates the association between the predicted phase of the lungs and the values of the cycle counter 401 such that imaging is performed at a timing earlier than the current values of the cycle counter 401, and at the same time, increases the frequency of auxiliary imaging.

Figure 10B:
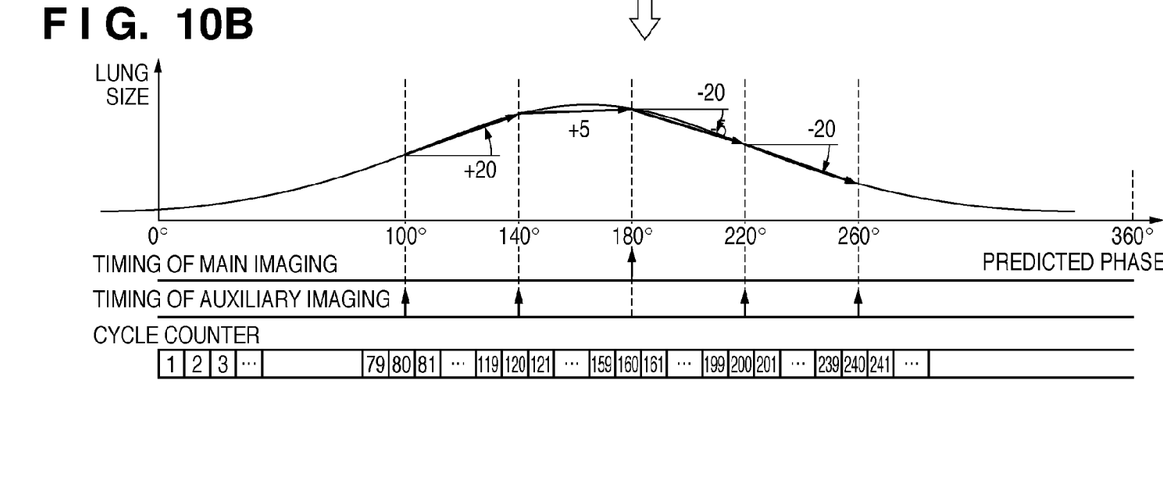

FIG. 10B shows an imaging timing in the cycle subsequent to that of FIG. 10A. Referring to FIG. 10B, in the predicted phase of the lungs, 20 cycles are subtracted from the respective values of the cycle counter of FIG. 10A, and each X-ray irradiation timing is generated at a timing earlier than that of the previous cycle. Furthermore, referring to FIG. 10B, the X-ray irradiation for the auxiliary imaging is generated at phases of 100°, 140°, 220° and 260°. By increasing the frequency of auxiliary imaging in the manner described here, the accuracy of phase detection is improved. Accordingly, the changed X-ray irradiation timings for auxiliary imaging are symmetric with respect to the phase of 180° at which main imaging is performed.

In the states of FIGS. 9B and 10B, if the result obtained by adding the amount of increase and the amount of decrease in lung size is smaller than a preset value, the frequency of auxiliary imaging is reduced. For example, if the absolute value of the amounts of increase and decrease in lung size is less than 25, the timing of auxiliary imaging is changed back to phases of 140° and 220° (the states of FIGS. 9A and 10A). In the descriptions given above, the frequency of auxiliary imaging, which is changed according to the result obtained through the addition of the amounts of increase and decrease in lung size, is set to two different times, namely, twice and four times. However, the present invention is not limited thereto. For example, the frequency of auxiliary imaging may be set to three different times, namely, twice, four times and six times. In this case, the interval of auxiliary imaging may be changed (e.g., the auxiliary imaging performed every 40° phase before and after the main imaging at the midpoint of the cycle is changed to auxiliary imaging performed every 35° phase before and after the main imaging at the midpoint of the cycle). Furthermore, in the above example, control is performed such that the state in which the organ is most expanded or most contracted is set as a particular phase, and imaging is performed at a timing corresponding to that particular phase. However, the particular phase is not limited thereto. The particular phase can also be set to any phase from when the organ is contracting or when the organ is expanding. In this case, when the sum of the amounts of increase and decrease in the size of the organ equals a particular value other than 0, it is determined that the predicted phase and the actual phase match.

By repeating the above process, main imaging is performed continuously in synchronization with a phase of 180° in which the lungs are most expanded. Even if a significant change occurs in the motion of the lungs during imaging, because the phase detection accuracy is improved by increasing the frequency of auxiliary imaging, the imaging timing can be corrected to follow the motion of the lungs. If imaging can sufficiently follow the motion of the object by increasing the frequency of auxiliary imaging, the amount of correction of imaging timing decreases, so that by decreasing the frequency of auxiliary imaging, the amount of radiation exposure to the subject can be minimized.

Figure 11:
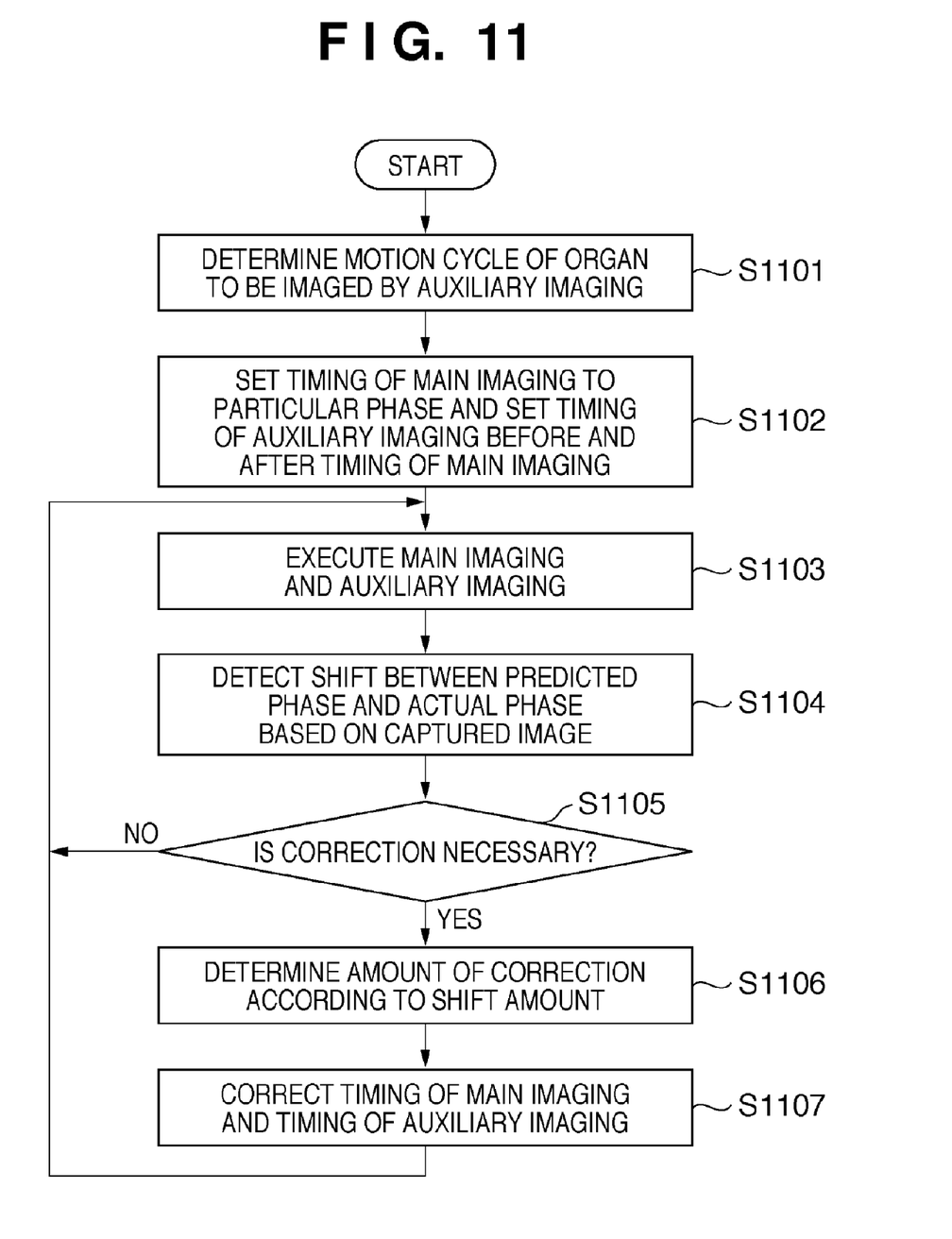
FIG. 11 is a flowchart used to illustrate an imaging process according to an embodiment of the present invention.

The process discussed above will be further described with reference to the flowchart of FIG. 11. First, in step S1101, the controller 107 detects the cycle of a periodically moving organ by executing auxiliary imaging. The method for detecting the motion cycle of an organ from captured images is well-known, thus, a description thereof is omitted herein (see Japanese Patent Laid-Open No. 2003-245272 and Japanese Patent Laid-Open No. 2005-342088). The cycle counter 401 increments its count value by one at the timing of each phase obtained by equally dividing the detected cycle into 360. As a result, the counter counts 0 to 360 (=0) in synchronization with the motion cycle of the organ. This count value is associated with each predicted phase (0° to 360°) in the cycle. Then, in step S1102, the phase at which main imaging is to be executed is set. In the example shown in FIGS. 5A to 7B, the particular phase at which main imaging is to be executed is set to 180°. The phase at which auxiliary imaging is to be executed is also set before and after the main imaging. In the example shown in FIGS. 5A to 7B, auxiliary imaging is performed twice each before and after the main imaging at an interval of 40°, so that the phase of auxiliary imaging is set to 100°, 140°, 220° and 260°.

In step S1103, the controller 107 executes main imaging and auxiliary imaging at the phases set above. Specifically, the timing generation unit 402 sends timing signals to the imaging control unit 112 such that main imaging is executed when the value of the cycle counter 401 is 180, and auxiliary imaging is executed when the value of the cycle counter 401 is 100, 140, 220 and 260. The imaging control unit 112 controls the X-ray generation unit 104 and the sensor unit 101 in response to the timing signals from the timing generation unit 402. Through this, main imaging as a first imaging in which radiographic imaging is performed with a first dose is executed at a timing predicted to correspond to a phase of 180°. Auxiliary imaging as a second imaging in which radiographic imaging is performed with a second dose that is less than the first dose is executed at timings predicted to correspond to phases of 100°, 140°, 220° and 260°. In step S1103, main imaging is performed on the periodically moving organ to be imaged at a timing predicted to correspond to a particular phase, and auxiliary imaging is performed a predetermined number of times before and after that predicted timing. With the repetition of the main imaging in step S1103, a plurality of X-ray images of the same phase are acquired.

Next, in step S1104, the motion detection unit 403 and the phase comparison unit 404 detect a shift between the phase timing recognized from a plurality of X-ray images obtained through the main imaging and the auxiliary imaging and the predicted phase timing. In the present embodiment, the sum of the amounts of increase and decrease in organ size is calculated as a shift amount. In step S1105, the timing correction unit 405 determines whether it is necessary to correct the timing based on the magnitude of the shift (the magnitude of the sum of the amounts of increase and decrease) detected by the phase comparison unit 404. In the present embodiment, the necessity of the correction is determined through the comparison between the sum of the amounts of increase and decrease in organ size and a predetermined value. If correction of the imaging timing is unnecessary, the process returns to step S1103, where imaging is repeated at the current timing.

If it is determined in step S1105 that it is necessary to correct the imaging timing, the process advances to step S1106. In step S1106, the timing correction unit 405 determines the amount of correction of the timing based on the detected shift amount. In step S1107, the timing correction unit 405 corrects the count values associated with the predicted timings corresponding to phases of 100°, 140°, 180°, 220° and 260° for the main imaging and auxiliary imaging described above. In the present embodiment, 20 is added to or subtracted from the count value of the predicted timing corresponding to each phase, depending on whether the predicted phase is delayed or advanced (see FIGS. 6A and 6B, and FIGS. 7A and 7B).

In the present embodiment, the amounts of increase and decrease in the size of the organ between images acquired by executing the main imaging and auxiliary imaging are detected, and the predicted timing is corrected such that the sum of the detected amounts of increase and decrease equals a predetermined value (0 in the present embodiment).

It is also possible to employ a configuration in which, in step S1107, the frequency of auxiliary imaging and the interval of auxiliary imaging are changed based on the shift amount detected in step S1106. It is also possible to change the amount of change in the timing of main imaging based on the shift amount. For example, it is conceivable that, if the absolute value of the shift amount is 30 or greater, the amount of change in the timing of main imaging is controlled to be ±20, and if the absolute value of the shift amount is from 25 to less than 30, the amount of change in the timing of main imaging is controlled to be ±15.

The relationship between the shift amount and the amount of change in the timing of main imaging can be appropriately set according to the organ to be imaged, etc. In this case, "relationship between shift amount and timing of main imaging" for each organ is stored in the form of a table, and when the user selects an organ at the time of imaging, "relationship between shift amount and timing of main imaging" to be used is determined.

As described above, with the X-ray fluoroscopy diagnostic apparatus for medical use according to the present embodiment, X-ray radiographic imaging with quality sufficient for surgery and diagnosis can be performed while suppressing the amount of X-ray exposure. Furthermore, according to the present embodiment, images obtained through the auxiliary imaging, in which imaging is performed by irradiating X-ray pulses at a dose lower than that used to obtain X-ray moving images for fluoroscopic diagnosis, are used for phase detection, so that even if the frame rate is high, the amount of radiation exposure to the subject can be suppressed to the minimum. Furthermore, even if the frame rate is lowered to reduce the amount of radiation exposure to the subject, the imaging timing can be corrected according to a change in motion to synchronize with the phase. Accordingly, imaging can be performed at an optimal timing all the time.

Other Embodiments

An embodiment of the present invention has been described in detail above, but the present invention can take the form of a system, apparatus, program, method, program, storage medium, etc. Specifically, the present invention may be applied to a system configured of a plurality of devices or to an apparatus configured of a single device.

The case where the functions of the above-described embodiment are achieved by directly or remotely supplying a software program to a system or apparatus and loading and executing the supplied program code through a computer in the system or apparatus also falls within the scope of the present invention. In this case, the supplied program is a computer program corresponding to the flowchart indicated in the drawings in the embodiment.

Accordingly, the program code itself that is installed in a computer to implement the functional processing of the present invention through the computer also realizes the present invention. In other words, the computer program itself for realizing the functional processing of the present invention also falls within the scope of the present invention.

In this case, a program executed through object code, an interpreter, script data supplied to an OS, etc., as long as it has the functions the program.

Examples of the storage medium that can be used to supply the computer program include floppy disks, hard disks, optical disks, magneto-optical disks, MOs, CD-ROMs, CD-Rs, CD-RWs, magnetic tape, non-volatile memory cards, ROMs, and DVDs (DVD-ROMs, DVD-Rs).

Alternatively, using a browser of a client computer to connect to an Internet website and downloading the computer program of the present invention to a recording medium such as a hard disk can be given as another method for supplying the program. In this case, the downloaded program may be a compressed file including a function for automatic installation. Furthermore, this method may be realized by dividing the program code that constitutes the program of the present invention into a plurality of files and downloading each file from different websites. In other words, a WWW server that allows a plurality of users to download the program files for realizing the functional processing of the present invention through a computer also falls within the scope of the present invention.

Furthermore, the program of the present invention may be encrypted, stored in a storage medium such as a CD-ROM, and distributed to a user. In this case, a user that has satisfied a predetermined condition is allowed to download key information for decryption from a website via the Internet, execute the encrypted program using the key information, and install the program on a computer.

In addition to the case where a computer realizes the functions of the above-described embodiment by executing a loaded program, the functions of the embodiment may be implemented in cooperation with an OS or the like running on the computer based on the instructions of the program. In this case, the OS or the like performs part or all of the actual processing, and the functions of the above-mentioned embodiment are realized by that processing.

Furthermore, a program loaded from the storage medium is written into a memory provided in a function expansion board installed in a computer or in a function expansion unit connected to the computer, whereby part or all of the functions of the above-described embodiment may be realized. In this case, after the program has been written into the function expansion board or the function expansion unit, a CPU or the like included in the function expansion board or the function expansion unit performs part or all of the actual processing based on the instructions of the program.

According to the present invention, when radiographic imaging a periodically moving tissue at a timing synchronized with the motion phase, the radiographic imaging can be performed at an optimal timing while suppressing the amount of radiation exposure.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-208472, filed on Aug. 9, 2007, which is hereby incorporated by reference herein in its entirety.

What is claimed is:

1. A radiographic imaging apparatus comprising:
an imaging unit configured to perform a first imaging in which radiographic imaging is performed with a first X-ray dose and a second imaging in which radiographic imaging is performed at a second X-ray dose that is less than the first X-ray dose;
a first execution unit configured to execute the second imaging on a periodically moving organ, wherein the first execution unit executes the second imaging at plural timings in one cycle of the periodically moving organ to obtain a plurality of images;
a determination unit configured to determine a predicted timing corresponding to a particular phase in the cycle of the periodically moving organ based on changing amounts acquired from the plurality of images obtained by the first execution unit; and
a second execution unit configured to execute the first imaging at the predicted timing determined by the determination unit.

2. The apparatus according to claim 1, further comprising:
a detection unit configured to detect a shift between the predicted timing and a timing corresponding to the particular phase that is recognized based on images acquired through the first and second imaging; and
a correction unit configured to correct the predicted timing based on the shift,
wherein the execution unit executes the second imaging before and after the predicted timing.

3. The apparatus according to claim 2,
wherein the detection unit detects amounts of increase and decrease in a size of the periodically moving organ between images acquired through the first and second imaging, and
wherein the correction unit corrects the predicted timing such that a sum of the amounts of increase and decrease in the size of the organ equals a predetermined value.

4. The apparatus according to claim 2,
further comprising a change unit configured to change the frequency of the second imaging based on an amount of the shift.

5. A method for controlling a radiographic imaging apparatus that performs a first imaging in which radiographic imaging is performed with a first X-ray dose and a second imaging in which radiographic imaging is performed at a second X-ray dose that is less than the first X-ray dose, the method comprising:
a first executing step of executing the second imaging on a periodically moving organ, wherein the first executing step executes the second imaging at plural timings in one cycle of the periodically moving organ to obtain a plurality of images;
a determining step of determining a predicted timing corresponding to a particular phase in the cycle of the periodically moving organ based on changing amounts acquired from the plurality of images obtained by the first executing step,
a second executing step of executing the first imaging at the predicted timing determined by the determining step.

6. The method according to claim 5, further comprising:
detecting a shift between a timing corresponding to the particular phase that is recognized based on images acquired through the first and second imaging and the predicted timing; and
correcting the predicted timing based on the shift,
wherein the execution step executes the second imaging before and after the predicted timing.

7. The method for controlling a radiographic imaging apparatus according to claim 6, wherein detecting the shift includes detecting, amounts of increase and decrease in a size of the periodically moving organ between images acquired through the first and second imaging, and
wherein, correcting the predicted timing includes correcting the predicted timing such that a sum of the amounts of increase and decrease equals a predetermined value.

8. The method for controlling a radiographic imaging apparatus according to claim 6, further comprising a changing the frequency of the second imaging based on an amount of the shift.

9. A non-transitory computer-storage medium storing a computer program for causing a computer to control a radiographic imaging apparatus that performs a first imaging in which radiographic imaging is performed with a first X-ray dose and a second imaging in which radiographic imaging is performed at a second X-ray dose that is less than the first X-ray dose, the computer program comprising:

a first executing step of executing the second imaging on a periodically moving organ, wherein the first executing step executes the second imaging at plural timings in one cycle of the periodically moving organ to obtain a plurality of images; and a determining step of determining a predicted timing corresponding to a particular phase in the cycle of the periodically moving organ based on changing amounts acquired from the plurality of images obtained by the executing step, wherein the executing step executes the first imaging at the predicted timing determined by the determining step; and a second executing step of executing the first imaging at the predicted timing determined by the determining step.

* * * * *